(12) United States Patent
Bange et al.

(10) Patent No.: US 7,531,304 B2
(45) Date of Patent: May 12, 2009

(54) METHOD FOR SCREENING FGFR-4 AGONISTS

(75) Inventors: Johannes Bange, Neuried (DE); Axel Ullrich, Munich (DE)

(73) Assignee: Max-Planck-Gesellschaft zur Foerderung der Wissenschaften E.V., Munich (DE)

( * ) Notice: Subject to any disclaimer, the term of this patent is extended or adjusted under 35 U.S.C. 154(b) by 109 days.

(21) Appl. No.: 10/503,242

(22) PCT Filed: Jan. 30, 2003

(86) PCT No.: PCT/EP03/00953

§ 371 (c)(1),
(2), (4) Date: Mar. 10, 2005

(87) PCT Pub. No.: WO03/063893

PCT Pub. Date: Aug. 7, 2003

(65) Prior Publication Data

US 2005/0153878 A1    Jul. 14, 2005

Related U.S. Application Data

(60) Provisional application No. 60/353,831, filed on Jan. 31, 2002.

(30) Foreign Application Priority Data

Jan. 31, 2002   (EP)   .................................. 02002358

(51) Int. Cl.
   *C12Q 1/68*      (2006.01)
   *G01N 33/53*     (2006.01)
   *A61K 38/18*     (2006.01)

(52) U.S. Cl. .............................. 435/6; 435/7.2; 514/12; 514/44

(58) Field of Classification Search .................. None
    See application file for complete search history.

(56) References Cited

U.S. PATENT DOCUMENTS 6,214,795 B1   4/2001   Benjamin et al.

FOREIGN PATENT DOCUMENTS

| FR | 2796073 | 1/2001 |
| WO | WO 9420125 | 9/1994 |
| WO | WO 9821237 | 5/1998 |
| WO | WO 9937299 | 7/1999 |
| WO | WO 0039311 | 7/2000 |

OTHER PUBLICATIONS

Ballinger et al., Semirational design of a potent, artificial agonist of fibroblast growth factor receptors, 1999, Nature Biotechnology, vol. 17, pp. 1199-1204.*
Bange et al., Cancer progression and tumor cell motility are associated with the FGFR4 Arg 388 allele, 2002, Cancer Research, vol. 62, pp. 840-847.*
Stadler et al., FGFR4 Gly388 isotype suppresses motility of MDA-MD-231 breast cancercells by EDG-2 gene repression, 2006, Cellular Signaling, vol. 18, pp. 783-794.*
A. Saito et al. "An overexpression of fibroblast growth factor (FGF) and FGF receptor 4 in a severe clinical phenotype of facioscapulohumeral muscular dystrophy" Muscle & Nerve, vol. 23, No. 4, Apr. 2000, pp. 490-497.
K. Hart et al., "Transformation and Stat activation by derivatives of FGFR1, FGFR3, and FGFR4," Oncogene, vol. 19, No. 29, Jul. 6, 2000, pp. 3309-3320.
C. Johnston et al., "Fibroblast growth factor receptors (FGFRs) localize in different cellular compartments," The Journal of Biological Chemistry, vol. 270, No. 51, Dec. 22, 1995, pp. 30643-30650, Baltimore, MD, USA.
M. Ballinger et al., "Semirational design of a potent, artificial agonist of fibroblast growth factor receptors," Nature Biotechnology, vol. 17, No. 12, Dec. 1999, pp. 1199-1204, New York, NY, USA.
Nygren et al., Journal of Immunological Methods, 290, 2004, 3-28.
Binz et al., Nature Biotechnology, vol. 23, Oct. 2005, 1257-1268.
Hey et al., Trends in Biotechnology, vol. 23, Oct. 2005, 515-522.
Williams et al., Neuron, Sep. 1994, 13(3):583-94.
Cavallaro et al., Nature Cell Biology, vol. 3, 2001, 650-657.
Huang et al., Molecular Carcinogenesis, vol. 45, 2006, 934-942.
Xie et al., "FGF-19, A Novel Fibroblast Growth Factor With Unique Specificity For FGFR4", Cytokine, vol. 11, No. 10 (Oct. 1999), pp. 729-735.
McLeskey et al., "MDA-MB-134 Breast Carcinoma Cells Overexpress Fibroblast Growth Factor (FGF) Receptors and are Growth-inhibited by FGF Ligands", Cancer Research, vol. 54, (Jan. 15, 1994), pp. 523-530.

* cited by examiner

*Primary Examiner*—Robert Landsman
*Assistant Examiner*—Ian Dang
(74) *Attorney, Agent, or Firm*—Millen, White, Zelano, Branigan, P.C.

(57) ABSTRACT

The present invention relates to the use of Fibroblast-Growth Factor Receptor (FGFR) agonists for the diagnosis, prevention and/or treatment of pathological conditions including, but not limited to hyperproliferative disorders, bone diseases and vascular diseases. Particularly, the use of FGFR-4 agonists, e.g. anti-FGFR-4 antibodies is described. Further, the invention relates to a pharmaceutical composition comprising the agonist as described above and a screening procedure.

9 Claims, 4 Drawing Sheets

METHOD FOR SCREENING FGFR-4 AGONISTS

Figure 1:
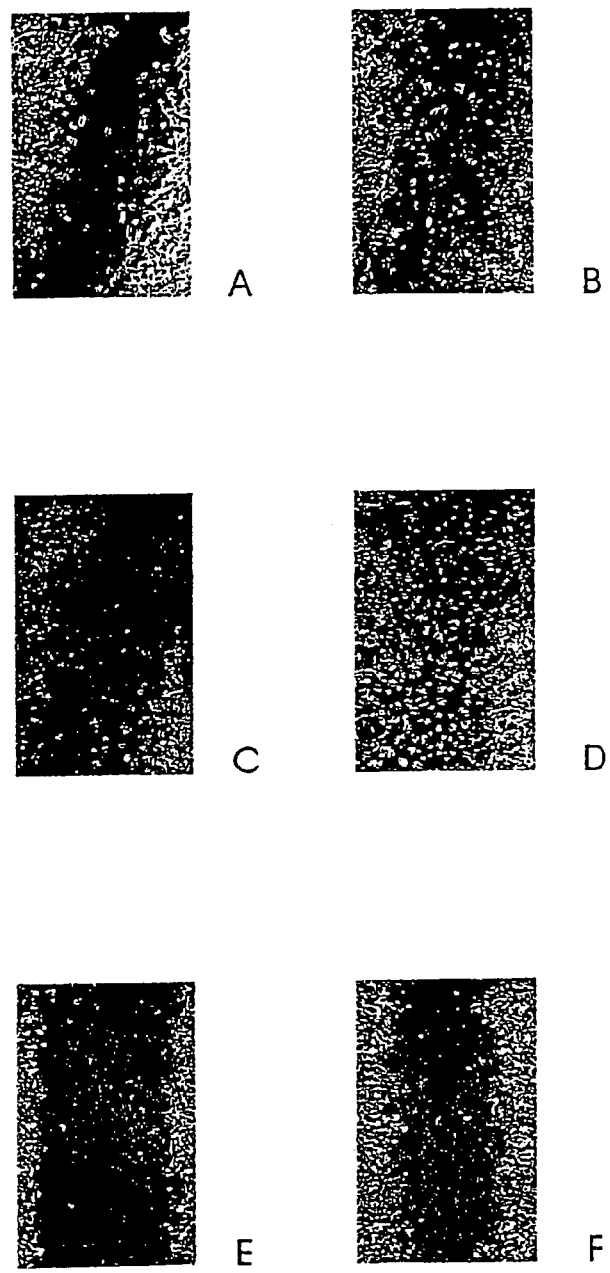

This application is a 371 of PCT/EP03/00953, filed Jan. 30, 2003, which claims priority to provisional application 60/353,831, filed Jan. 31, 2002.

The present invention relates to the use of Fibroblast-Growth Factor Receptor (FGFR) agonists for the diagnosis, prevention and/or treatment of pathological conditions including, but not limited to hyperproliferative disorders, bone diseases and vascular diseases. Particularly, the use of FGFR-4 agonists, e.g. anti-FGFR-4 antibodies is described. Further, the invention relates to a pharmaceutical composition comprising the agonist as described above and a screening procedure.

WO99/37299 discloses the use of FGFR inhibitors for the treatment and/or prevention of disorders associated with FGFR over function, particularly cancer.

Surprisingly, it was found that in many cases not FGFR inhibitors but selective FGFR activators are suitable for the prevention and/or treatment of hyperproliferative disorders, since these agonists stimulate cell differentiation processes.

Thus, the invention relates to the use of a compound which is capable of stimulating the activity of an FGFR species for the manufacture of a therapeutic or diagnostic agent, e.g. an agent for the prevention and/or treatment of pathological conditions, e.g. hyperproliferative disorders, particularly neoplastic diseases.

At present four structurally related FGFR genes are known which encode four different proteins, namely FGFR-1, -2, -3, and -4. The FGFR proteins exhibit an extracellular domain consisting of three immunoglobulin loops and an acidic portion, a hydrophobic transmembrane domain and an intracellular domain exhibiting tyrosine kinase activity. Different isoforms are known for FGFR-1, FGFR-2 and FGFR-3 which may result e.g. from alternative splicing. At least two allelic variants exist for FGFR-4, which differ at amino acid position 388 (cf. WO99/37299), i.e. FGFR-4 Gly388 and FGFR-4 Arg388.

The FGFR agonist compound preferably stimulates the activity of an FGFR species which is selected from the group consisting of FGFR-1, FGFR-2, FGFR-3 and FGFR-4. More preferably, the FGFR species is FGFR-4. Preferably, the stimulation is selective, i.e. the stimulation of an FGFR species as described above does not lead to a significant stimulation of other FGFR species. In this context "significant stimulation" means that the agonistic compound is not able to stimulate the biological activity of other FGFR molecules in a physiologically relevant scope. It should be noted, however, that for some embodiments a selectivity for only one FGFR species may not be required, i.e. the agonist may stimulate two or even more FGFR species, wherein the degree of stimulation may be about the same or different for individual species.

In a first embodiment the compound exhibits its stimulatory activity by binding to an FGFR species, i.e. it binds to an FGFR species selected from FGFR-1, FGFR-2, FGFR-3 and particularly FGFR-4 or isoforms or allelic variants thereof and thereby increases the FGFR activity. Especially preferred the activity of FGFR-4 Gly388 is increased. The compound preferably shows a selective stimulation of an FGFR species. More preferably, the compound does not cross-react with different FGFR species, i.e. it binds selectively to a given FGFR species. It should be noted, however, that for some embodiments a selectivity may not be required.

The binding compound may be a natural or synthetic FGFR ligand, which possesses the required binding selectivity. For example FGF-19 (Xie et al.) has a high selectivity to bind to FGFR-4. On the other hand, the binding compound may be an anti-FGFR antibody, which specifically binds to an FGFR species, e.g. FGFR-4 and has no significant cross reactivity to other FGFR species. A suitable antibody is described in the examples. The term "antibody" according to the present invention comprises monoclonal antibodies and chimeric or humanized antibodies derived therefrom by known techniques, human antibodies, recombinant antibodies such as single chain antibodies or antibody fragments such as Fab, F(ab)$_2$, Fab' antibody fragments or recombinant antibody fragments such as scFv fragments, provided they exhibit selective and agonistic binding to an FGFR species as described above. Furthermore, the binding compound may be a scaffold protein having antibody-like binding characteristics.

By binding to the FGFR species the compound increases the biological activity of the receptor, e.g. a tyrosine kinase activity, the ability to interact with other proteins, e.g. to promote cell-cell contacts and/or other interactions with FGFR "downstream targets", e.g. proteins. More particularly, the tyrosine phosphorylation of the FGFR species is increased. The increase of tyrosine kinase activity may be determined, e.g. by immunoprecipitation of the FGFR species and subsequent determination using suitable anti-phosphotyrosine antibodies as described in the examples.

In a second embodiment, the FGFR activity is stimulated by an indirect interaction. The compound may bind to or otherwise interact with an "upstream target", e.g. a protein different from FGFR, but which is capable of stimulating FGFR activity.

In a third embodiment, the FGFR activity is stimulated by increasing the gene dosage, e.g. by administering and/or over-expressing an FGFR gene, particularly an FGFR-4 gene and more particularly the FGFR-4 Gly388 gene in the target cell or target organism. This embodiment preferably comprises a gene-therapeutic approach wherein the FGFR gene is introduced into the target cell by means of a suitable vector, e.g. a viral or nonviral gene transfer vector as known in the art.

The design of FGFR agonists and other means for stimulating FGFR activity is described by Ballinger et al. (Nature Biotech 17 (1999), 1199-1204); WO 98/21237; FR-A-2796073; and WO 00/39311, which are herein incorporated by reference. None of these documents, however, suggest that FGFR activation results in a decrease in tumorigenicity.

The invention is based on the surprising finding that the stimulation of FGFR activity leads to a decrease of tumor size in vivo in a mouse model. Consequently, the stimulation of FGFR activity may be used for the prevention and/or treatment of FGFR-associated disorders such as hyperproliferative disorders, e.g. neoplastic disorders such as colon, kidney, bladder, pancreas, prostate, gastric, breast, lung, thyroid, pituitary, adrenal and ovarian tumors or glioblastomas, leukemias, as well as thyroid hyperplasia, retinitis pigmentosa, precocious puberty, acromegaly and asthma. Further examples are bone diseases such as osteoporosis and vascular diseases such as restinosis, artherosclerosis and high blood pressure.

Thus, the invention relates to a method for preventing and/or treating a disorder associated with FGFR dysfunction, particularly associated with an at least partial lack of FGFR activity comprising administering a subject in need thereof a compound in a sufficient amount which stimulates FGFR activity. Particularly, the present invention also relates to a method for preventing and/or treating a disorder associated with FGFR dysfunction, particularly associated with an at least partial lack of FGFR activity comprising administering a subject in need thereof a compound in a sufficient amount which exhibits selective binding to an FGFR species and is capable of stimulating FGFR activity by binding thereto. The subject is preferably a mammal and more preferably a human. For medical purposes the compound is usually administered as a pharmaceutically acceptable composition, which may contain suitable diluents, carriers and/or adjuvants. The composition may also contain further pharmaceutically active agents, e.g. cytotoxic agents for the treatment of cancer.

Pharmaceutical compositions suitable for use in the present invention include compositions wherein the active ingredients are contained in an effective amount to achieve its intended purpose, e.g. a therapeutic or diagnostic purpose. A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g. for determining the LD50 (the dose lethal to 50% of the population) and the ED50 (the dose therapeutically effective in 50% of the population). For any compound used in the method of the invention, the therapeutically effective dose can be estimated initially from cell culture assays. For example, a dose can be formulated in animal models to achieve a circulating concentration range that includes the IC50 as determined in cell culture (i.e. the concentration of the test compound which achieves a half-maximal inhibition of the growth-factor receptor activity). Such information can be used to more accurately determine useful doses in humans. The dose ratio between toxic and therapeutic effects is the therapeutic index and it can be expressed as the ratio between LD50 and ED50. Compounds which exhibit high therapeutic indices are preferred. The exact formulation, route of administration and dosage can be chosen by the individual physician in view of the patient's condition (see e.g. Fingl et al., 1975, in "The Pharmacological Basis of Therapeutics", Ch. 1, p. 1).

Dosage amount and interval may be adjusted individually to provide plasma levels of the active moiety which are sufficient to maintain the receptor modulating effects, or minimal effective concentration (MEC). The MEC will vary for each compound but can be estimated from in vitro data, e.g. the concentration necessary to achieve a 50-90% inhibition of the receptor using the assays described herein. Compounds should be administered using a regimen which maintains plasma levels above the MEC for 10-90% of the time, preferably between 30-90% and most preferably between 50-90%. Dosages necessary to achieve the MEC will depend on individual characteristics and route of administration. In cases of local administration or selective uptake, the effective local concentration of the drug may not be related to plasma concentration.

The actual amount of composition administered will, of course, be dependent on the subject being treated, on the subject's weight, the severity of the affliction, the manner of administration and the judgement of the prescribing physician.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systematic manner, for example, via injection of the compound directly into a solid tumor, often in a depot or sustained release formulation.

Furthermore, one may administer the drug in a targeted drug delivery system, for example in a liposome coated with a tumor-specific antibody. The liposomes will be targeted to and taken up selectively by the tumor.

In a different embodiment the pharmaceutical composition may be a diagnostic composition. In a preferred embodiment a diagnostic composition comprises a diagnostic reagent to determine expression of an FGFR species in a target cell or target organism. The expression may be determined on protein level, e.g. by using anti-FGFR antibodies and/or by determining FGFR activity. On the other hand, FGFR expression may be determined on nucleic acid level, e.g. by determining FGFR mRNA, for example by an RT-PCR protocol or another suitable detection protocol known in the art.

Still a further aspect of the present invention is a method for identifying novel inhibitors of pathological conditions, e.g. hyperproliferative processes in cells or organisms, particulary mammalian cells or organisms, e.g. human cells or organisms, comprising:

testing the ability of a compound to
(1) exhibit binding to an FGFR species and preferably
(2) stimulate the FGFR activity by binding thereto.

The method may be carried out as a high throughput screening procedure which may be a cell-based assay using an FGFR expressing or overexpressing cell or a cell-free assay using substantially or particularly purified FGFR protein. The assay is suitable for identifying novel compounds or classes of compounds having the desired properties, e.g. from libraries of biological or synthetic compounds. Further, the present invention encompasses any novel inhibitor identified by the disclosed method.

The ability of test compounds to exhibit the desired properties can be determined as described in the examples.

Finally, the invention relates to a cell line capable of producing an agonistic anti-FGFR antibody as described above. The cell line may be a eukaryotic or prokaryotic cell line, e.g. mammalian cell line, particularly a lymphoid cell line, e.g. a hybridoma cell line, or a CHO cell line. Further, the cell may be an insect cell line, a plant cell line, a eukaryotic unicellular organism, e.g. a yeast, or a bacterium, particularly a gram-negative bacterium such as *E. coli*. The cell line is suitable for the manufacture of an agonistic anti-FGFR antibody as described above.

FIGURE LEGENDS

FIGS. 1A-F

MDA-MB-231 breast cancer cells (ATCC HTB-26) Expressing human FGFR-4 Gly388 show reduced migration in a wound assay. Confluent monolayers of cells infected with retroviruses containing either vector control (A, B), FGFR-4 Arg388 (C, D) or FGFR-4 Gly388 cDNAs (E, F) were scraped with a plastic tip and incubated with 0% FCS (A, C, E) or 0.5% FCS (B, D, F). After 24 h, numerous individual control and FGFR-4 Arg388 cells have migrated into the wound (B, D), in contrast to FGFR-4 Gly388 cells, which show only a few individual cells in the wound (F).

FIG. 2:

L6 Myoblasts (ATCC CRL-1458) expressing human FGFR-4 were either stimulated with 1 and 10 µg/ml 4FA6D3C10 or the same amount of control antibody (α-C) for 10 min. Cell lysates were subjected to immunoprecipitation (IP) using polyclonal anti-FGFR-4 (α-FGFR-4) antibodies. Tyrosine phosphorylation level was analysed by western blotting (WB) with monoclonal anti-phosphotyrosine antibody (α-PY) (upper panel). Equal loading of proteins was checked by reblotting with α-FGFR-4 antibodies (lower panel).

FIG. 3:

The number of viable MCF7 breast cancer cells ectopically expressing human FGFR-4 (MCF7/FGFR4-clone 1 and -clone 2) can be decreased by treatment with ligands aFGF and bFGF.

FIG. 4:

The number of viable BT549 breast cancer cells ectopically expressing human FGFR-4 (BT549/FGFR4-clone 1 and -clone 2) can be decreased by treatment with ligands aFGF and bFGF.

EXAMPLE 1

To address the role of FGFR-4 expression in tumor cell migration, we ectopically expressed human FGFR-4 Gly388 and FGFR-4 Arg388 isoforms in human breast cancer cells. Appropriate FGFR-4 cDNAs were amplified from MDA-MB-453 cells (ATCC HTB-131) and K562 cells (ATCC CCL-243), respectively, and subcloned into the Bluescript I KS vector (Stratagene) according to standard protocols (Current Protocols). Both cDNAs were cloned into the pLXSN vector (Stratagene). The packaging cell line *Phoenix* A (gift of Prof. Nolan, Stanford University), that produces amphotrophic viruses was transfected with these vectors using calcium phosphate DNA coprecipitation. The supernatant of transfected *Phoenix* A cells was collected and filtered through a 0.45 µm filter. Cells infected with the vector pLXSN alone were used as controls.

For infection of the human breast cancer cell line MDA-MB-231, which does not express detectable amounts of FGFR-4, cells were incubated with viral supernatant for 24 h. After 48 h, medium was replaced with medium containing 400 µg/ml G418 and further selected under G418 for 14 days.

Clonal cells lines were generated by limited dilution. FGFR-4 expression was determined by western blot analysis. For each FGFR-4 isoform, FGFR-4 Gly388 and FGFR-4 Arg388, respectively, two clonal cell lines showing similar expression levels of FGFR-4 were chosen for further analysis. In an analogous manner mouse NIH-3T3 (ATCC CRL-1658) and rat L6 myoblasts were infected with supernatants from an ectotrophic virus producing cell line GF+E 86 (Markowitz et al., 1988) resulting in the cell lines NIH-3T3/huFGFR-4 and L6/huFGFR-4, respectively.

We next examined migration of MDA-MB-231 breast cancer cells using a scratch wound method (Hutenlochner et al., 1998). Cells were grown in a confluent monolayer and migration during wound closure was studied after a wound was gently scraped with a plastic tip. The medium was removed and cells were washed twice with PBS. Medium without fetal calf serum (FCS) or medium with 0.5% FCS was added, and the cells were permitted to scatter/migrate into the cleared area for 24 h. Surprisingly, in comparison to control MDA-MB-231 cells, the wound closure rate was decreased in cell cultures overexpressing FGFR-4 Gly388 (FIG. 1). In contrast, control virus infected cells or cells expressing the FGFR-4 Arg388 migrated in a scattered fashion into the wound. Thus the MDA-MB-231 cells expressing the FGFR-4 Gly388 show inhibition of cell migration.

To determine, whether the effects of FGFR-4 on the in vitro tumor phenotype translate to in vivo effects on tumorigenicity, we assessed the role of FGFR-4 expression on tumor growth in mice. Seven- to ten-week-old female Balb/c nu/nu mice, bred in the animal facilities of the Max-Planck-Institut, Martinsried, Germany, were used for the assays. They were kept in specified pathogen-free conditions. Their care and housing were in accordance with German laws and supervised by authorized investigators. Freshly trypsinized semiconfluent MDA-MB-231 cell clones expressing either FGFR-4 Gly388 or FGFR-4 Arg388 or control cells were suspended in phosphate buffered saline (PBS) at a concentration of $2.8 \times 10^7$ cells/ml. Each mouse was inoculated subcutaneously in the neck region with four million cells (140 µl cell suspension+60 µl Matrigel; 13 µg/ml). For both FGFR-4 Gly388 and FGFR-4 Arg388 two individual clonal cell lines were selected and injected into sets of 5-8 animals as described above, Tumor formation was monitored for up to six weeks. Thereafter, or whenever the tumor diameter reached a size of 1 cm$^3$ animals were sacrificed. Tumor sizes were measured three times per week using calipers, and tumor volume was estimated using the formula length× width$^2$/2.

As summarized in Table 1, mice injected with control cells that expressed neither FGFR-4 Gly388 nor FGFR-4 Arg388 receptor formed tumors within one week and mean tumor size after four weeks was 1 cm$^3$. Surprisingly, in 12 out of 13 mice injected with FGFR-4 Gly388 expressing cells no tumor growth was observed, suggesting that FGFR-4 Gly388 caused complete inhibition of tumor formation thus acting as a tumor suppressor. No tumors were detected in the monitoring period of six weeks. Interestingly, cells expressing the FGFR-4 Arg388 isoform caused tumors in 80% and 62.5% of injected mice. However, the size of the tumors formed by these cells was significantly smaller than the size of tumors formed by control cells infected with the pLXSN vector alone. In addition, the tumors resulting from injection with the FGFR-4 Arg388 expressing clones all grew more slowly than tumors derived from control cells. Thus, although FGFR-4 Arg388 is less active in suppressing tumor growth than FGFR-4 Gly388, it still conferred a significant advantage compared to a lack of FGFR-4 expression.

These results demonstrate that specific activation of the FGFR-4 has the potential to block and/or inhibit tumor progression. Therefore our next investigations concentrated on the generation of monoclonal antibodies against the extracellular domain of FGFR-4 and the use thereof in the activation of FGFR-4. To this end a recombinant Glutathione-S-Transferase (GST) (Smith & Johnson, 1988) fusion protein comprising the FGFR-4 extracellular domain (FGFR-4 ex) was prepared. We used the cloning vector pSj26(mod) (Seiffert et al., 1999) that was designed for the eukaryotic expression and secretion of recombinant fusion proteins and was derived from the pCDNA3 cloning vector (Invitrogen, Groningen, The Netherlands) by inserting the complete DNA sequence coding for *Schistosoma japonicum* glutathione-S-transferase (GST) (Pharmacia Biotech, Freiburg, Germany) in the Xho1 and Apa1 sites of pCDNA3.

The extracelluar domain of FGFR-4 was PCR amplified using the following primers: sense: AAGAATTCGCCAC-CATGCGGCTGCTGCTGGCCCTGTTG (SEQ ID NO. 1), antisense: CGAGGCCAGGTATACGGACATCATC-CTCGA GTT (SEQ ID NO.2). The PCR product was digested with EcoR1 and Xho1 and cloned into pSj26(mod). The resulting pSj26(mod)-FGFR-4ex expression plasmid was transfected into 293 cells (ATCC CRL-1573) by the calcium phosphate DNA coprecipitation method. Cells were grown in Dulbecco's modified Eagle's medium (DMEM) supplemented with 10% FCS. After selection with 1 mg/ml G418 (Sigma, Deisenhofen, Germany) for two weeks, surviving clones were tested for expression and secretion of the fusion protein by Western blot analysis with antibodies against GST. High-expressing cells were used to produce FGFR-4ex. Medium was collected from confluent cultures every two days. One liter of collected medium was sterile fitered and incubated with 1 ml glutathione Sepharose (Pharmacia Biotech, Freiburg, Germany) overnight at 4° C. The Sepharose was separated and washed with phosphate-buffered saline (PBS). Elution was performed with 5 ml 10 mmol/l glutathione at 20° C. Eluted fusion protein was dialyzed $1:10^6$ (vol/vol) in PBS/10% glyerol. Protein concentration was determined using MicroBCA protein determination kit (Pierce, Rockford, Ill.).

Monoclonal antibodies were raised by immunization of four- to eight-week-old female Balb/c mice with purified recombinant FGFR-4-GST fusion protein as described before containing the whole extracellular domain of FGFR-4. The mice were injected intramuscularly 3 times in 14-day intervals with 50 µg protein diluted 1:2 in ABM-2 adjuvants (Pan-Systems, Aidenbach, Germany). The spleens were removed 4 days after the last injection for fusion with the SP2/0 myeloma cell line. The resulting hybridomas were grown in RPMI 1640 culture medium containing 10% FCS, antibiotics, and hypoxanthine, aminopterin, and thymidine (HAT) (Sigma). Culture supernatants were screened by flow cytometry on NIH-3T3/huFGFR-4 cells (see above), and positive hybridomas secreting antibodies that selectively recognize the transfectant, but not the parental NIH-3T3 cells were cloned by limiting dilution. A FGFR-4-reactive clone (4FA6D3C10) was cultured in serum-free medium supplemented with 1% Nutridoma (Roche, Germany), and antibodies were purified from supernatants using Protein G-Sepharose columns (Pharmacia Biotech, Freiburg, Germany).

In order to assess the functional role of 4FA6D3C10 on FGFR-4 activation L6/huFGFR-4 cells were either left untreated or stimulated with 10 and 20 µg/ml 4FA6D3C10 for 10 min at 37° C. Cells were lysed on ice in lysis buffer (50 mM HEPES pH 7.5, containing 150 mM NaCl, 1 mM EDTA, 10% (v/v) glycerol, 1% (v/v) Triton X-100, 1 mM sodium fluoride, 1 mM phenylmethylsulfonyl fluoride, 1 mM sodium orthovanadate, 1 mM β-glycerolphosphate, 10 µg/ml aprotinin). Crude lysates were centrifuged at 12500 g for 20 min at 4° C. Overexpressed FGFR-4 was immunoprecipitated by polyclonal FGFR-4 antibody (Santa Cruz) and 30 µl of protein A-Sepharose (Pharmacia) which were added to the cleared lysate and incubated for 3 h at 4° C. Immunoprecipitates were washed with a washing buffer (20 mM HEPES pH 7.5, containing 150 mM NaCl, 1 mM EDTA, 1 mM sodium fluoride 10% (v/v) glycerol, 1% (v/v) Triton X-100). Sample buffer containing SDS and 2-mercaptoethanol was added and the samples were denatured by heating at 95° C. for 4 min.

Proteins were fractionated by SDS-PAGE and transferred to nitrocellulose fiters. To determine the level of tyrosine phosphorylation of FGFR-4, nitrocellulose filters were incubated with the phosphotyrosine specific mouse monoclonal antibody 4G10 (Upstate Biotechnology) at 4° C. Next, a HRP-coupled goat anti-mouse or goat anti-rabbit secondary antibody was added, followed by an enhanced chemiluminescence (ECL) substrate reaction (Amersham, Germany). The substrate reaction was detected on Kodak X-Omat film. To ensure equal amounts of immunoprecipitated FGFR-4 protein filers were stripped according to the manufacturer's protocol (Amersham, Germany), blocked and reprobed with polyclonal FGFR-4 antibody.

Figure 2:
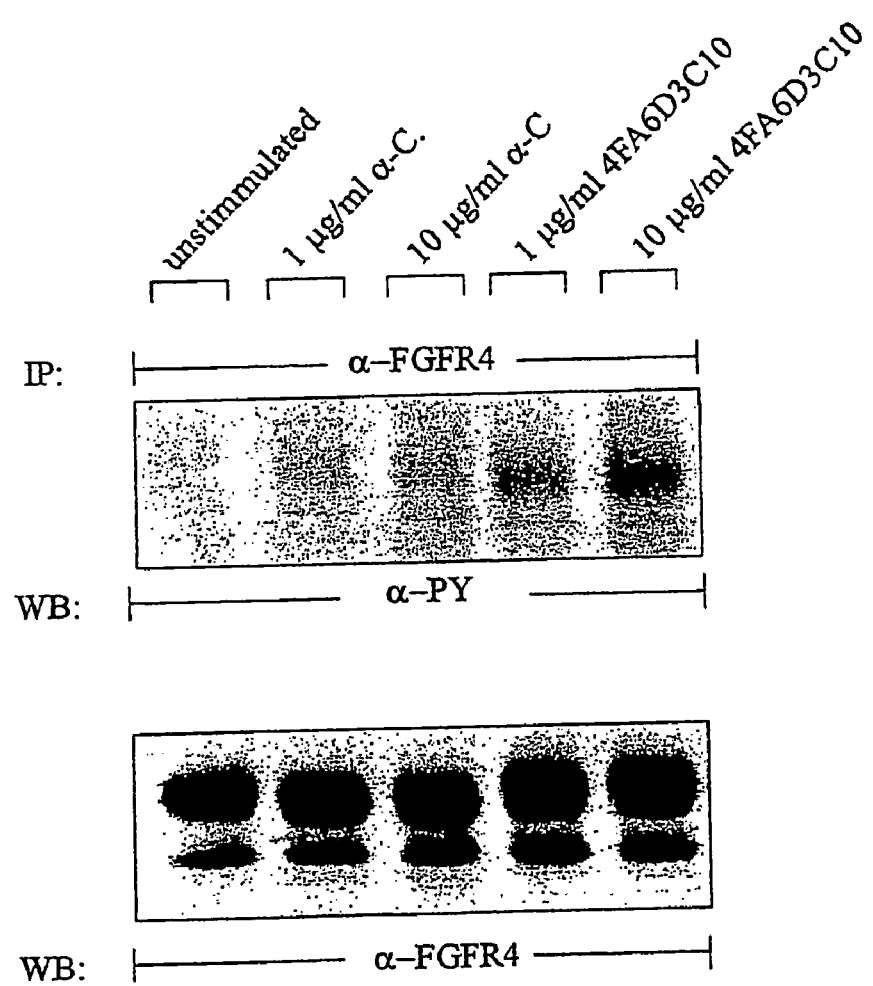

Treatment of L6/huFGFR-4 cells with 4FA6D3C10 leads to a significant increase of the FGFR-4 tyrosine phosphorylation as shown in FIG. 2. These data demonstrate that a monoclonal antibody and in particular 4FA6D3C10 can be used for FGFR-4 receptor activation.

TABLE 1

| Cells | Genotype | Number of injected mice/tumors |
|---|---|---|
| MDA-MB-231 plx | no FGFR-4 expression | 12/13 |
| MDA-MB-231 WT2 | Gly/Gly | 1/5 |
| MDA-MB-231 WT3 | Gly/Gly | 0/8 |
| MDA-MB-231 MT6 | Arg/Arg | 4/5[a] |
| MDA-MB-231 MT11 | Arg/Arg | 5/8[a] |

Table 1:

$4 \times 10^6$ cells were inoculated in each mouse subcutaneously in the neck region (140 µl cell suspension+60 µl Matrigel; 13 µg/ml). Tumor growth was monitored every 2-3 days. Animals were sacrificed after six weeks or whenever the tumor diameter reached a size of 1 cm³. [a] The size of the tumors formed by these cells was significantly smaller than the size of tumors formed by control cells infected with the pLXSN vector alone. plx: control cells, WT: FGFR-4 Gly388; MT: FGFR-4 Arg388.

EXAMPLE 2

Although FGFR4 and its ligands is expressed in a number of human cancer cell lines, the role of FGFR4 in the regulation of human tumor development has not been fully investigated. To analyze the function of FGFR4 in regulating tumor growth of human cancer cells, we utilized the human breast cancer cells lines BT549 and MCF7 ectopically expressing human FGFR4.

Breast cancer cells MCF7 cells were plated in triplicates in 12 well plates, at 5000 cells/500 µl medium supplement with 10% FCS and incubated for 24 h. Cells were stimulated with 10 ng/ml aFGF and bFGF or 25 ng/ml beta-Heregulin in 1% FCS and grown over a period of 6 days. In the case of the breast cancer cell line BT549, cells were plated in sextuplicates in 96-wells dishes, at 1000 cells/100 µl in normal growth medium (DMEM, 10% FCS; 0.065% Insulin 40 U/ml) and incubated for 24 h. Medium was removed and cells were treated with 10 ng/ml aFGF, bFGF or 25 ng/ml beta-Heregulin for 72 h without FCS and insulin. Proliferation was assayed using the non-radioactive AlamarBlue assay (Biosource). Briefly, AlmarBlue was added in an amount equal to 10% ot the culture volume and incubated for 2 hours at 37° C. Fluorescence was measured at 544 nm excitation wavelength and 580 nm emission wavelength. For comparative purposes, values were calculated and presented as percentage of control (unstimulated cells).

Figure 3:
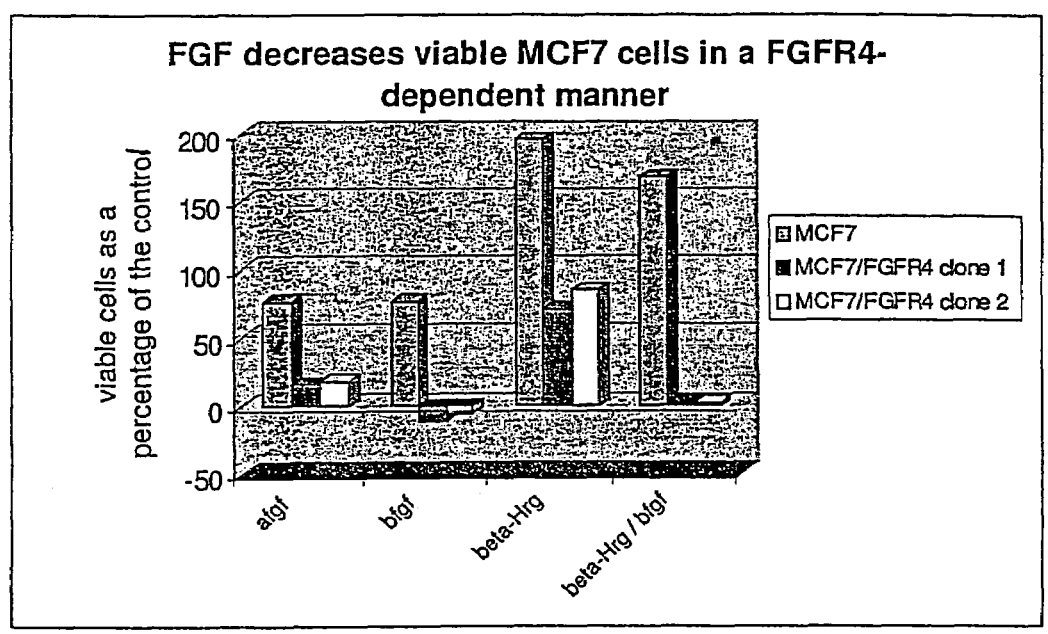
Figure 4:
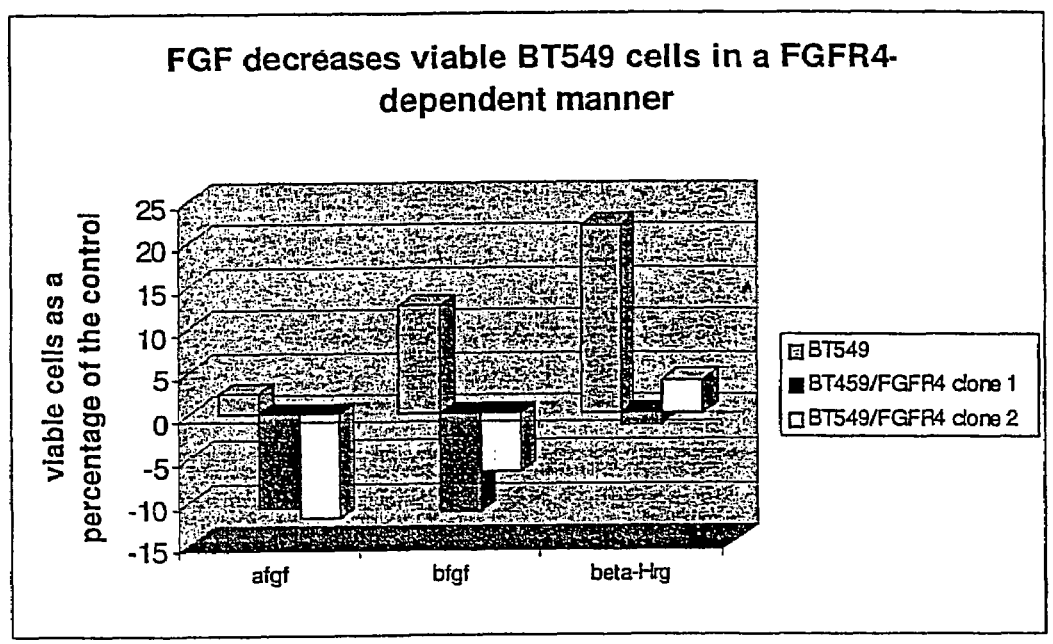

As shown in FIG. 3 aFGF or bFGF stimulation of MCF7 cells infected with a empty vector leads to a significant increase of viable cells. In addition, treatment with beta-Heregulin or beta-Heregulin and bGFG simultaneously activates cell proliferation. However exposure of MCF7 cells ectopically expressing FGFR4 (MCF7 FGFR4-clone 1, -clone 2) with aFGF or bFGF results in reduced cell growth. Moreover proliferation of BT549 breast cancer cells expressing FGFR4 is reduced when stimulated with aFGF, bFGF or beta-Heregulin (FIG. 4) whereas cell proliferation of BT549 control cells is not affected. Therefore FGFR4 functions as an inhibitor of MCF7 and BT549 breast cancer cells.

LITERATURE

Ausubel, F. M., Brent, R., Kingston, R. E., Moore, D. D., Seidman, J. G., Smith, J. A. and Struhl, K. (eds.), Current Protocols in Molecular Biology. Wiley, 1987, 1997.

Huttenlochner, A., Lakonishok, M., Kinder, M., Wu, S., Truong, T., Knudsen K. A., Horwitz, A. F., Integrin and cadherin synergy regulates contact inhibition of migration and motile activity. J. Cell Biol. 1998 Apr. 20, 141(2):515-26.

Smith, D. B. and Johnson, K. S., Single-step purification of polypeptides expressed in *Escherichia coli* as fusions with glutathione S-transferase Gene 67(1):31-40 (1988).

Markowitz, D., Goff, S., Bank, A., A safe packaging line for gene transfer: separating viral genes on two different plasmids. J. Virol. 1988 April; 62(4):1120-4.

Seiffert, M., Cant, C., Chen, Z., Rappold, I., Brugger, W., Kanz, L., Brown, E. J., UlLrich A., Buhring, H. J., Human signal-regulatory protein is expressed on normal, but not on subsets of leukemic myeoloid cells and mediates cellular adhesion involving its counter receptor CD47. Blood. 1999 Dec. 1;94(11):3633-43.

Xie, M. H., Holcomb, I., Deuel, B., Dowd, P., Huang, A., Vagts, A., Foster, J., Liang, J., Brush, J., Gu, Q., Hillian K., Goddard, A., Gurney, A. L., FGF-19, a novel fibroblast growth factor with unique specificity for FGFR-4. Cytokine. 1999 October; 11(10):729-35.

We claim:

1. A method for screening a compound which is capable of stimulating the activity of a Fibroblast Growth-Factor Receptor species 4 (FGFR-4) for the manufacture of a diagnostic or therapeutic agent comprising
    measuring the ability of said compound to
    (1) bind to said FGFR-4 species and
    (2) stimulate the tyrosine kinase activity of said FGFR-4 by binding thereto, wherein said FGFR-4 species is human FGFR-4 Gly388 or human FGFR-4 Arg388, and wherein said method is carried out as a cell-based assay using an FGFR-4 expressing said or overexpressing cell or as a cell-free assay using said FGFR-4 species protein.

2. The method of claim 1, wherein the FGFR-4 is FGFR-4Gly388.

3. The method of claim 1, wherein the FGFR-4 is FGFR-4 Arg388.

4. The method of claim 1, wherein the compound is natural.

5. The method of claim 1, wherein the compound is a synthetic FGFR-4 ligand.

6. The method of claim 1, wherein the compound is an antibody or a scaffold protein which specifically binds to said FGFR-4 species.

7. The method of claim 1, wherein the compound interacts with an upstream target of said FGFR-4.

8. The method of claim 1, wherein said assay is a high-throughput assay.

9. A method for screening a compound which is capable of stimulating the activity of a Fibroblast Growth-Factor Receptor species 4 (FGFR-4) which is human FGFR-4 Gly388 or human FGFR-4 Arg388 comprising
    employing a cell which expresses or overexpresses said FGFR-4 species and
    measuring the ability of said compound to
    (1) bind to said FGFR-4 species and
    (2) stimulate the tyrosine kinase activity of said FGFR-4 species.

SEQUENCE LISTING

<160> NUMBER OF SEQ ID NOS: 2

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence:primer

<400> SEQUENCE: 1
aagaattcgc caccatgcgg ctgctgctgg ccctgttg                    38

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:primer

<400> SEQUENCE: 2
cgaggccagg tatacggaca tcatcctcga gtt                         33

* * * * *